United States Patent [19]

Forrester

[11] Patent Number: 4,827,775
[45] Date of Patent: May 9, 1989

[54] APPARATUS FOR EXTRACTING A SAMPLE

[76] Inventor: Gilbert Forrester, 10/62 Alexandra Street, Hunters Hill, N.S.W. 211, Australia

[21] Appl. No.: 74,691

[22] Filed: Jul. 17, 1987

[51] Int. Cl.<sup>4</sup> ............................................. G01N 1/14
[52] U.S. Cl. ............................. 73/864.33; 73/863.81
[58] Field of Search ............ 73/864.33, 863.81, 863.21

[56] References Cited

U.S. PATENT DOCUMENTS

| | | | |
|---|---|---|---|
| 3,685,345 | 8/1972 | Wise | 73/864.33 X |
| 3,747,411 | 7/1973 | McDermott et al. | 73/864.33 X |
| 3,786,682 | 1/1974 | Winter et al. | 73/864.33 X |
| 4,762,009 | 8/1988 | Scrudto | 73/863.21 X |

FOREIGN PATENT DOCUMENTS

48793/85  7/1987  Australia.
106765  4/1984  European Pat. Off..

Primary Examiner—Tom Noland
Attorney, Agent, or Firm—Andrus, Sceales, Starke & Sawall

[57] ABSTRACT

An apparatus for extracting a sample of fibrous particles from a liquid suspension comprising a nozzle adapted to be connected to a supply of pressurized liquid and an inlet funnel connected to a sample delivery tube. Both the nozzle and the funnel are immersed in the suspension and the nozzle is directed into the inlet of the funnel.

5 Claims, 2 Drawing Sheets ies of fibrous or threadlike particles suspended in a
APPARATUS FOR EXTRACTING A SAMPLE This invention relates to apparatus for obtaining samples of fibrous or threadlike particles suspended in a liquid and, in particular, to apparatus for extracting a sample from a stream of such material.

BACKGROUND OF THE INVENTION

The manufacture of a number of products including paper, paper board, fibre board and non-woven fabrics involves a step in which the particles used to form the end product are suspended in a liquid transporting medium. It is often desirable to determine various physical parameters of the particles while they are suspended in the transporting liquid. For this purpose it is necessary to obtain a representative sample of the particles. Normally, only a sample of the particles and not the liquid is required. A particular example of the need to obtain a representative sample for analysis is to be found in the paper making industry. In this regard Australian patent application no. 48793/85 discloses a method and apparatus for making paper in which a sample of fibrous stock taken from a liquid suspension is analysed to provide information for adjustment of refining means used to process the stock.

An inherent difficulty confronts any attempt to obtain a representative sample of fibrous particles from a suspension thereof, due to the tendency of such particles to agglomerate by entanglement so as to block any orifice through which a sample of the suspension may be drawn. That difficulty may to a certain extent be overcome by agitating the bulk suspension by mechanical means to effect a mixing and disentanglement of the particles. However, even within an agitated vessel there may be eddies or currents which act to separate particles having different physical properties. A human operator can be used to offset this problem by taking a sample from an agitated part of the vessle, however, this introduces further problems of accessibility, safety and consistency of sampling technique. Moreover, this technique does not lend itself to automation so that continuous sampling can be effected.

Very often the liquid and particle mixtures of interest are pumped through pipelines during the various stages of production. At the center of such a pipeline the motion of the particles is relatively uniform, free of eddies and settling does not occur. Accordingly, a sample drawn from the central region of the pipeline will be relatively typical of the particles travelling in the stream of material. As the pressure within a pipeline conveying fluid is normally higher than external pressure, a small sampling aperture provided, for example, by means of a tube extending to the center of the pipeline should result in a sample being forced through the tube to the exterior of the pipeline. In practice however, unless the sampling aperture is very large compared to the dimension to the particles suspended in the liquid, bridging or blocking of the sampling aperture can occur. Any such bridging or blocking will result in the sampling becoming selective and not representative of the actual particle distribution in the liquid, or may interrupt sampling flow entirely.

SUMMARY OF THE INVENTION

It is an object of this invention to provide an apparatus for extracting a sample of fibrous particles from a liquid suspension thereof which will overcome, or substantially ameliorate, the abovementioned disadvantages.

Accordingly, this invention consists in apparatus for extracting a sample of fibrous particles from a liquid suspension thereof, said apparatus comprising a nozzle adapted to be connected to a supply of pressurized liquid, and an inlet funnel connected to a sample delivery tube, said nozzle being directed into the inlet of the funnel.

For preference, the nozzle and inlet funnel are axially aligned.

In operation, a jet of the pressurized liquid is expelled from the nozzle and travels through the bulk suspension and into the inlet funnel. In this way particles from the suspension are entrained into the jet of liquid and are carried with the jet into the inlet funnel and the delivery tube.

The jet of liquid is preferably adjusted to provide a slightly larger flow than that which can be accepted by the funnel to result in a small turbulent backflow in the region where the jet enters the funnel.

Because a flow of pressurized liquid is continuously passing into the inlet funnel and because of the small turbulent backflow the funnel remains un-bridged or un-clogged by particles from the suspension.

DESCRIPTION OF THE DRAWINGS

One embodiment of this invention will now be described, by way of example only, with reference to the accompanying drawings in which.

DESCRIPTION OF THE ILLUSTRATED EMBODIMENT

Figure 1:
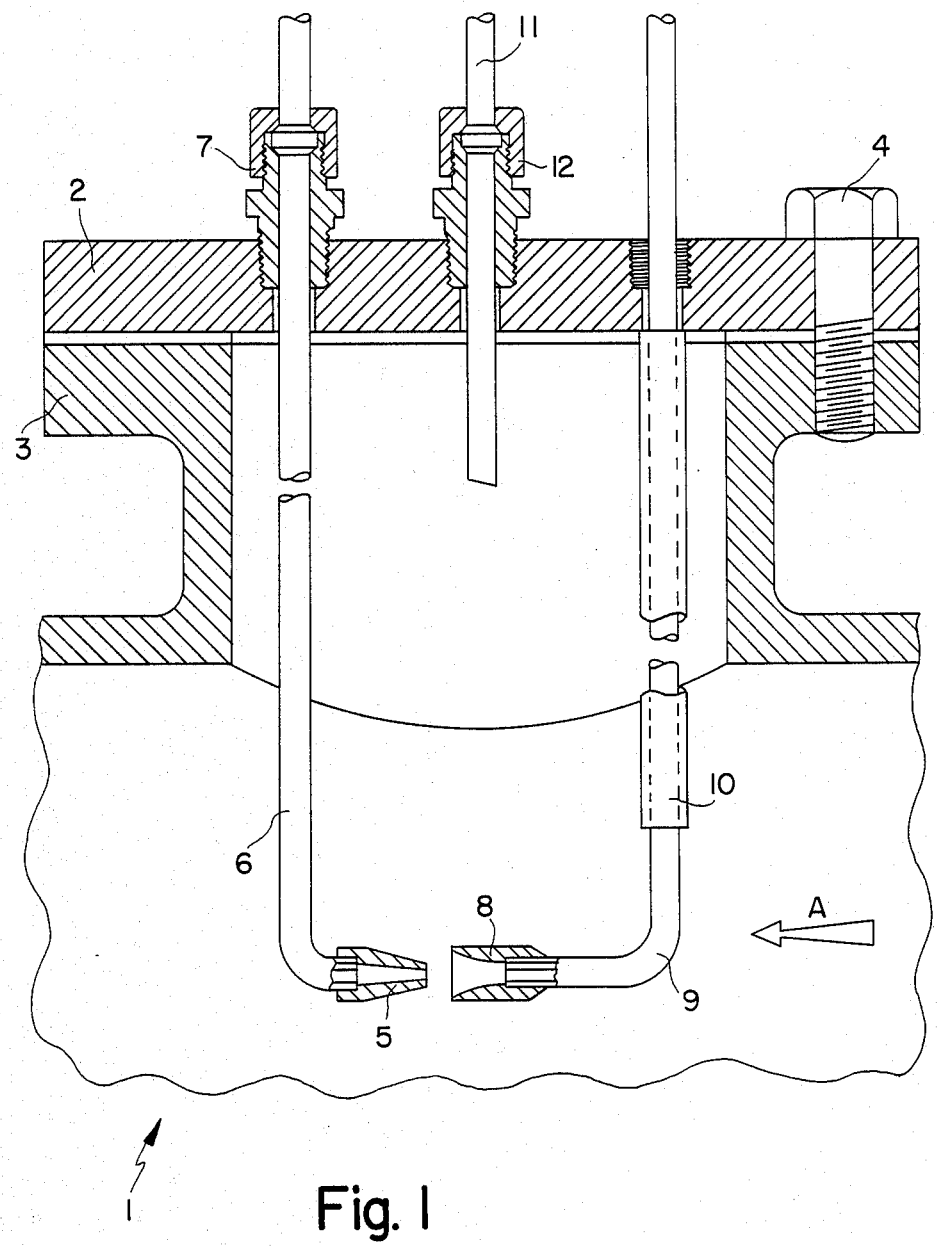
FIG. 1 is an elevation in part section of the apparatus of this invention fitted to a pipeline for conveying a stream of material.

As seen in FIG. 1 the apparatus of this invention is fitted to a Tee piece 1 forming part of a pipeline (not shown) carrying a stream of material (also not shown). The flow direction of the stream of material through Tee piece 1 is from right to left as viewed in FIG. 1 and shown by arrow "A".

The Tee piece 1 is positioned in the pipeline and sealed by a cap 2 held to the flange 3 of the Tee piece 1 by means of bolts 4. The apparatus of this invention comprises a nozzle 5 fixed to the end of a tube 6. The nozzle 5 is positioned at the center of the "through passage" of the pipeline by tube 6 being secured to cap 2 by means of a sealing connection 7. Nozzle 5 has a conical exterior shape and the inner flow surfaces thereof have smooth parabolic profiles. An inlet funnel 8 is fixed to the end of a delivery tube 9 which also extends from cap 2 and is secured thereto by means of a sealing connection (not shown). The exterior of inlet funnel 8 presented to the stream of material is smoothly curved to minimise flow disturbance and the internal flow passages of inlet funnel 8 also have smooth parabolic profiles. Nozzle 5 is connected via tube 6 to a supply of pressurized liquid (not shown) which can, for example, be a mains water supply.

A right angle bend in tube 6 adjacent nozzle 5 directs the nozzle upstream of the stream of material in the pipeline and into inlet funnel 8 which is axially aligned with nozzle 5 by means of a right angle bend in tube 9.

A reinforcing sleeve 10 is shown positioned over tube 9 to provide additional strength to tube 9 and thus maintain the position of the funnel 8. The additional strengthening is only required in certain applications and a similar sleeve can be fitted to tube 6 for the same purpose.

A return tube 11 is shown fitted to the center of cap 2 by means of sealing connection 12. The function of the return line will be explained below in connection with operation of an automatic sampling system.

In use the apparatus of this invention operates as follows. Pressurized liquid is supplied to nozzle 5 by means of tube 6. The liquid is expelled from the nozzle 5 and passes upstream through the stream of material into inlet funnel 8. This jet of liquid entrains particles from the flow which are carried with the jet as it is directed by funnel 8 into delivery tube 9. Delivery tube 9 thus contains a mixture of the pressurized liquid and a sample of particles from the stream of material.

Because the nozzle 5 is directed upstream of the stream of material, the only particles entering the throat of funnel 8 are those entrained by the jet of liquid. These fibers have been relatively separated and aligned by the action of the jet of liquid and thus enter the funnel without bridging or blocking. It has been found that this arrangement is most effective in extracting particles continuously from suspensions containing high particle densities without any blockage.

To prevent agglomerations of the particles in the funnel 8 the jet of liquid can be adjusted to supply a larger flow than can be accepted by the funnel 8. In this way the excess liquid from the jet results in a back flow which separates agglomerations before they are drawn into the funnel 8.

By adjusting the pressure of the supplied liquid and thus the flow of the liquid jet, the particles entrained into delivery tube 9 may be driven some distance through the deliver tube to a testing station, for example.

Figure 2:
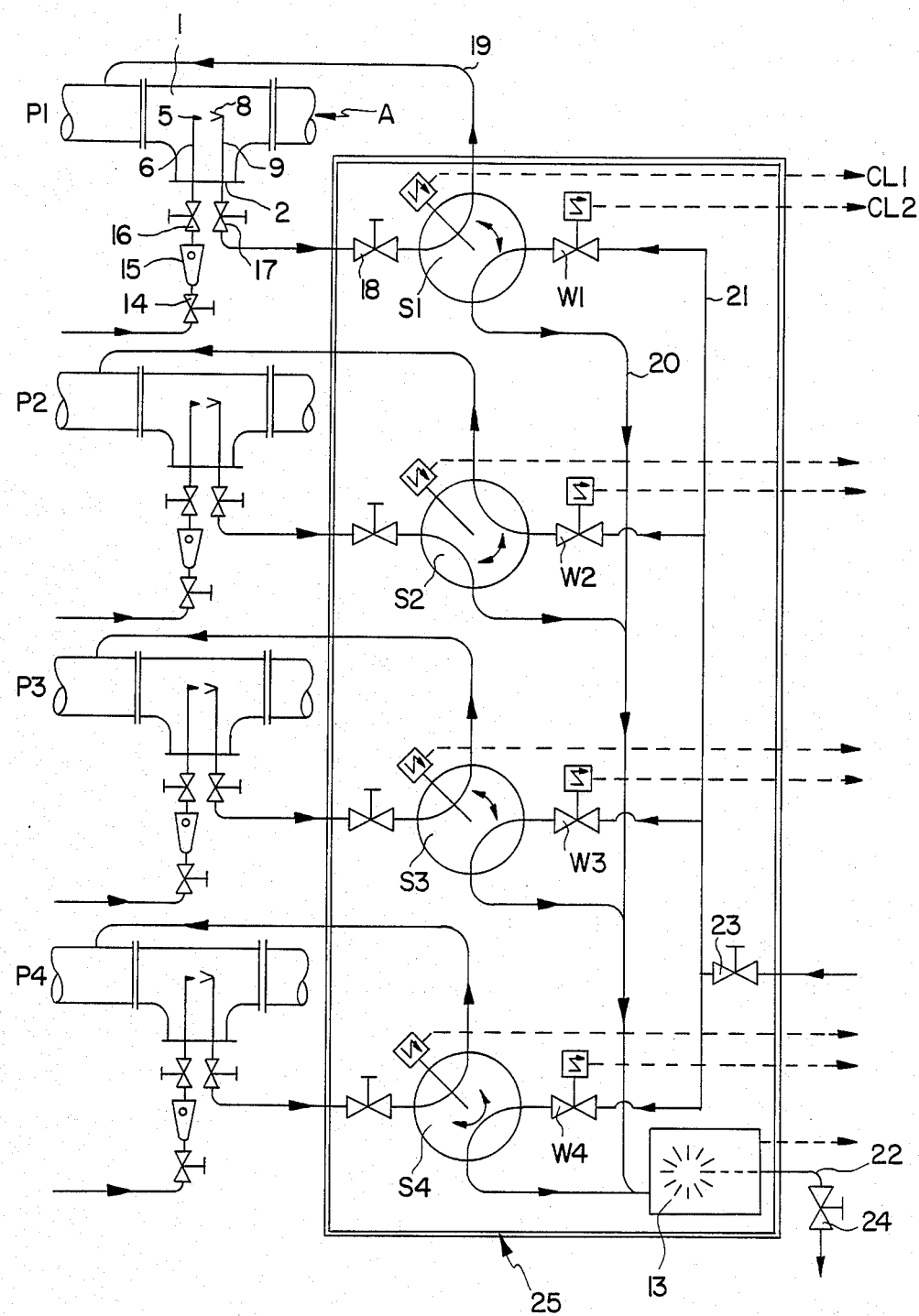
FIG. 2 is a schematic flow diagram of an automatic sampling system employing the sampling apparatus of this invention.

FIG. 2 illustrates an automatic sampling system employing the apparatus of this invention. The arrangement shown comprises four sampling apparatus of this invention each installed in one of four Tee pieces 1 in four separate pipelines P1, P2, P3 and P4. The four pipelines are illustrated to show how several of the sampling apparatus according to this invention can be connected in parallel to provide continuous sampling for a single particle analyzer 13. The arrangement and operation of each of the four parallel systems is identical and only one will described. The sampling apparatus is fitted in Tee piece 1 in the manner described above. A supply of fresh water is supplied to tube 6 and nozzle 5 via a control valve 14, a flow meter 15 and a second valve 16. Delivery tube 9 is connected via valve 17 and 18 to a four way solenoid actuated valve S1. Valves 16 and 17 are shut off valves provided for use when lines are disconnected and do not contribute to the operation of the invention. The valve S1 is operated in a conventional manner by means of an electric control line CL1. A return line 19 is provided from valve S1 to pipeline P1. This line is schematically illustrated as joining line P1 outside Tee piece 1 however a return line 11 to the Tee piece 1 can be used as illustrated in FIG. 1.

A supply line 20 provides a communication between valve S1 and analyzer 13. A fresh water supply line 21 is also connected to valve S1 and the supply of fresh water to the valve S1 is regulated by means of a solenoid control valve W1. The valve W1 is operated electrically via control line CL2 in a conventional manner. Fresh water is supplied to line 21 by means of a valve 23 connected to an appropriate supply. The valve 23 is an on/off supply valve and does not contribute to the operation of the system. A discharge line 22 is provided from analyzer 13 and is fitted with a valve 24. Valve 24 is optionally used to maintain a back pressure in line 20 relative to the pressure in pipeline P1. In practice, the tee piece and its associated inlet and outlet valves are installed in a mill pipeline and connected via valve 18 and return line 19 to the rest of the apparatus which is preferably housed in a protective enclosure 25 which may be located remotely.

In use the system operates as follows. Pressurized liquid is supplied via flow meter 15 to tube 6 and thus nozzle 5. The jet of water expelled from nozzle 5 entrains particles flowing in a stream in pipeline P1 and forces them through delivery tube 9 as described above. Valves 17 and 18 are normally open and a sample and liquid mixture is thus delivered to control valve S1 and directed into return line 19 to pipeline P1. When the sample from pipeline P1 is required to be directed to analyzer 13, valve S1 is operated to direct the flow from delivery tube 9 to line 20 which is connected with analyzer 13. In FIG. 2, valve S2 is illustrated in position to direct the sample from pipeline P2 to line 20, while water from line 21 is directed through the corresponding return line to pipeline P2. After analysis the sample is discharged via line 22. When an analysis of the sample from pipeline P1 is completed, control valve S1 is operated to again direct the flow from delivery tube 9 to return line 19. In this way the flow through the sampling apparatus is continued at all times to prevent clogging of the lines that might occur if particles were were allowed to settle.

When control valve S1 is actuated to connect delivery line 9 with return line 19 fresh water supply line 21 is connected with the delivery line 20 to analyzer 13. For a short period after each sampling operation control valve W1 is actuated to allow a flow of fresh water through line 20 and analyzer 13 to flush out the line and analyzer. The supply line 20 and analyzer 13 are thus in a clean condition ready to receive a sample from one of the other pipelines P2, P3 or P4.

When the apparatus of this invention is used in the making of paper to extract samples of fibrous stock from a suspension for analysis in accordance with the method of Australian patent application no. 48793/85, it has been found that a mains water supply provides a suitable source of pressurized liquid when used with a nozzle having a 1.5 mm outlet diameter and with a nozzle to funnel spacing of 3 mm.

It will be apparent that the sampling apparatus of this invention provides the advantage of being particularly suitable for use in an automatic sampling system as described above by providing a continuous typical sample from the stream of the material flowing in the pipeline to be selectively directed as required. The apparatus is also particularly suited to applications where it is desirable to continuously monitor the properties of particles rather than testing discrete samples obtained from time to time.

The claims defining the invention are as follows:

1. Apparatus for extracting a sample of fibrous particles from a liquid suspension thereof, said apparatus comprising a nozzle adapted to be connected to a supply of pressurized liquid, and an inlet funnel connected to a sample delivery tube, said nozzle being directed into the inlet of the funnel, in use both said nozzle and funnel being immersed in said suspension.

2. Apparatus according to claim 1 wherein said nozzle and inlet funnel are coaxially aligned.

3. Apparatus according to claim 1 claims wherein the nozzle is dimensioned to ensure when the apparatus is in use, that more liquid from said supply is emitted by said nozzle than may be taken in by said funnel.

4. Apparatus according to claim 1 wherein said nozzle and funnel are disposed within a pipeline along which said suspension may flow and wherein the nozzle is directed in a direction opposite to the direction of flow of the suspension.

5. A method of periodically examining a sample of fibrous particles in a liquid suspension flowing in a pipeline comprising the steps of continuously extracting a sample from the pipeline utilizing apparatus according to any one of the preceding claims, intermittently diverting part of the extracted sample to an inspection device and flushing the device clean between each such diversion.

* * * * *

UNITED STATES PATENT AND TRADEMARK OFFICE
CERTIFICATE OF CORRECTION

PATENT NO.   :   4,827,775
DATED        :   May 9, 1989
INVENTOR(S)  :   GILBERT FORRESTER

It is certified that error appears in the above-identified patent and that said Letters Patent is hereby corrected as shown below:

Col. 5, Line 5, CLAIM 3, After "1" delete ---claims---

Signed and Sealed this

Eleventh Day of December, 1990

Attest:

HARRY F. MANBECK, JR.

Attesting Officer

Commissioner of Patents and Trademarks